United States Patent [19]

Vletter

[11] Patent Number: Plant 7,152

[45] Date of Patent: Feb. 13, 1990

[54] *ERYNGIUM PLANUM* PLANT NAMED CALYPSO

[75] Inventor: Floris Vletter, Rijnsburg, Netherlands

[73] Assignee: de Vennootschap Onder Firma Gebr, Vletter & J.A. Den Haan, Netherlands

[21] Appl. No.: 260,726

[22] Filed: Oct. 21, 1988

[51] Int. Cl.[4] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffrey, Schwaab, Mack, Blumenthal & Evans

[57] ABSTRACT

A distinct cultivar of *Eryngium planum* named Calypso, discovered growing in a bed of plants of the parent cultivar Fluela. Calypso distinguishes from its parent by its longer peduncles, it variegated leaves comprised of cream colored margins and internal stripes or specks, and by its asexual reproducability only by tissue culture. The flower color of Calypso is medium violet, similar to its parent.

4 Drawing Sheets

1

The present invention comprises a new and distinct cultivar of *Eryngium planum,* commonly called sea holly, known by the cultivar name Calypso.

Calypso was discovered by the inventor Floris Vletter in Rijnsburg, the Netherlands on July 10, 1982 in a controlled environment. The new cultivar was discovered growing among plants of the parent cultivar Fluela, disclosed in the inventor's pending plant patent application. Calypso was particularly differentiated from its parent by its distinctly different rosette and stem leaves. As contrasted to the relatively dark green and glossy leaves of the parent, the leaves of Calypso are greyish green in base color and have formed on its leaf edges a relatively broad band or margin which is cream colored. The main greyish green portions of the leaves also have irregularly formed cream colored stripes or specks.

The first act of asexual reproduction of Calypso was accomplished by means of tissue culture on Oct. 5, 1983 in a controlled environment in Twyford, Great Britain by a technician supervised by applicant. To date, tissue culture has been the only successful method of asexual reproduction. Horticultural examination of selected units, initiated on Aug. 10, 1987 has demonstrated that the combination of characteristics as herein disclosed for Calypso are firmly fixed and are retained through successive generations of asexual reproduction.

Calypso has not been observed under all possible environmental conditions. The phenotype may vary considerably with variations in environment such as temperature, light intensity and day length. The following observations, measurements and comparisons describe plants grown in Wageningen, the Netherlands under outside conditions which approximate those generally used in commercial practice. Color references are made to The Royal Horticultural Society Colour Chart.

The accompanying photographic drawings show typical features of a specimen plant of the new cultivar, with colors being as true as possible for color illustrations of this type.

Photographic Sheet 1 shows a typical bloom stalk of the variety.

Photographic Sheet 2 is a closeup view of flowers of a typical specimen of the variety in full maturity.

2

Photographic Sheet 3 depicts the stem and foliage of a typical specimen of the variety.

Photographic Sheet 4 is a perspective view of the foliage of a typical specimen of the variety.

The following traits have been repeatedly observed and are determined to be basic characteristics of Calypso, which in combination distinguish this *Eryngium planum* as a new and distinct cultivar:

1. Variegated leaves, with both the rosette and stem leaves being greyish green in base color and having a cream colored margin, the non-marginal portions of the leaves additionally possessing irregularly formed cream colored specks or stripes.
2. Medium violet flower color.
3. Strong, relatively long peduncles that are somewhat spread to form a more rounded plant, with the peduncles having secondary and tertiary branches.
4. Calypso differs from its parent Fluela by its long peduncles and variegated leaves. The flower color is virtually the same as Fluela.
5. Calypso to date is asexually reproducible only by tissue culture.

Plant:

*Form.*—Relatively large.

*Size.*—About 90 cm tall when mature.

*Growth habit.*—Rosette is dense, and plant has large peduncles.

*Blooming habit.*—Branching flower heads.

Leaves:

*Size.*—Rosette leaves about 11 cm long, slightly glossy, with petioles of about 14 cm.

*Color.*—No precise color value exists. New leaves are lighter than 136B, maturing into a variegated leaf, the main body of which is 136B–C with a blue tinge on the margins, which are closest to 158B.

*Quantity.*—Approximately 25.

*Shape.*—Leaf almost elliptical, crenate, with leaf margin short pricked.

Peduncle:

*Size.*—From 45 cm upwards, branching out laterally, and formed with secondary and tertiary branches.

*Color.*—The main stem silvery green grey with a light purple-blue tinge increasing in intensity towards the top; lateral branches light purple-blue, about R.H.S. 86 B–C.

*Stem leaves.*—Stem leaves sessile, leaf blades at the base of the peduncle similar to those of the rosette leaves, upwards along the peduncle with deeper incisions and then palmately parted and pricked; color being greyish green in base similar to those of the rosette leaves.

Flowers:

*Size.*—Medium. Each flower is approximately 1.9 centimeters tall, with a width of 1.6 centimeters.

*Form.*—Almost ellipsoid; involucral leaves long and narrow, about R.H.S. 90 B–C.

*Number.*—The number of flowers depends on the root, varying from 40 to 80 flowers for each plant.

*Color.*—Upper surface: Petals and filaments violet, approximately 86 B–C.

Propagation: The new cultivar is reproduced through successive breeding generations by tissue cultivar.

I claim:

1. A new and distinct cultivar of *Eryngium planum* named Calypso, as illustrated and described.

* * * * *

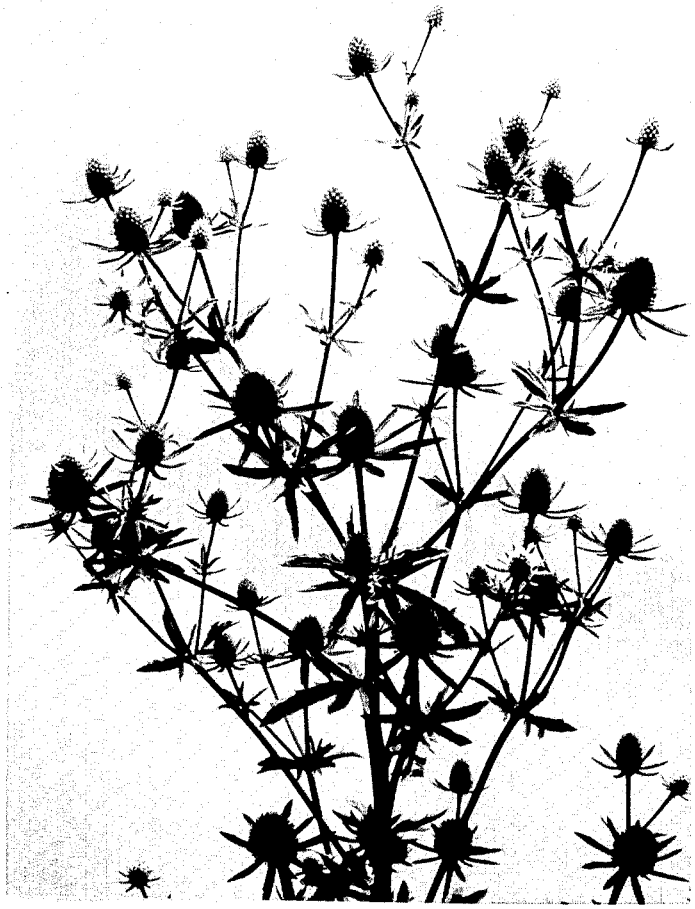

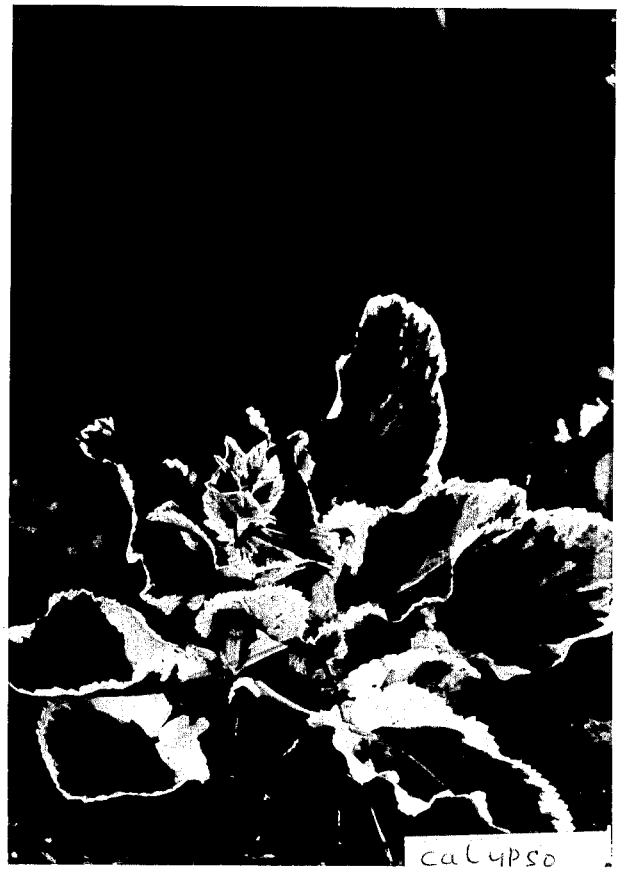
calypso

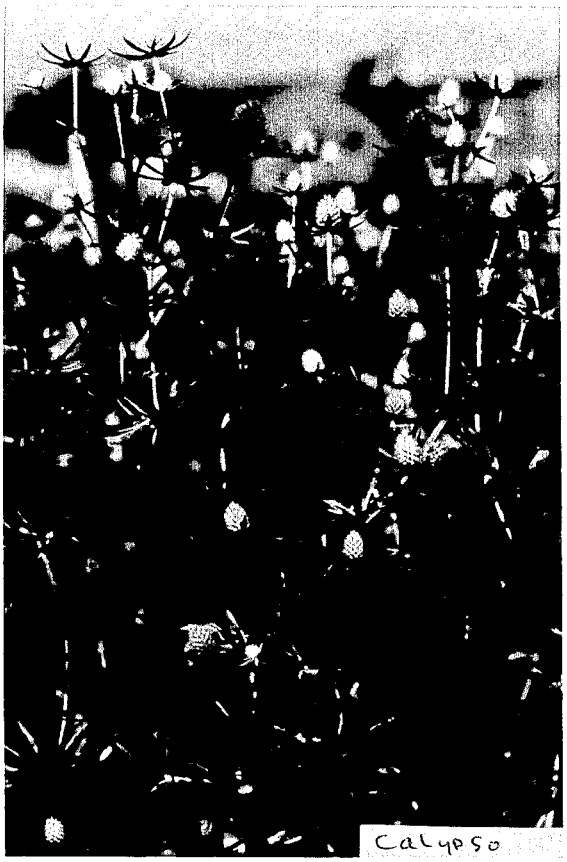
Calypso

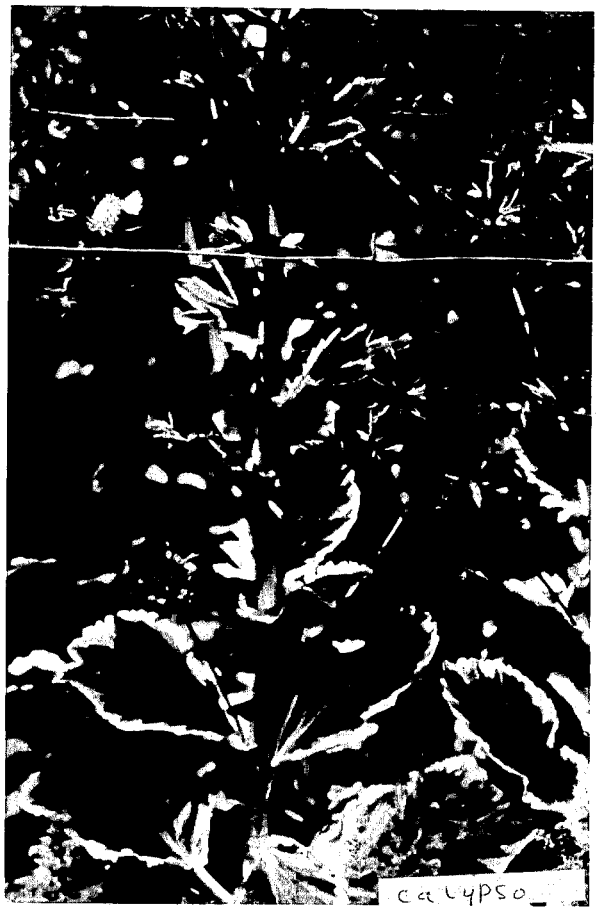
CALYPSO